United States Patent
Frojdh

(10) Patent No.: US 8,752,418 B2
(45) Date of Patent: Jun. 17, 2014

(54) DEVICE FOR REDUCING LOSS OF LIQUID DURING FRACTION COLLECTION

(75) Inventor: Hakan Frojdh, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 290 days.

(21) Appl. No.: 13/376,924

(22) PCT Filed: Jun. 4, 2010

(86) PCT No.: PCT/SE2010/050621
§ 371 (c)(1),
(2), (4) Date: Dec. 8, 2011

(87) PCT Pub. No.: WO2010/144036
PCT Pub. Date: Dec. 16, 2010

(65) Prior Publication Data
US 2012/0079896 A1    Apr. 5, 2012

(30) Foreign Application Priority Data
Jun. 9, 2009    (SE) ...................... 0950430

(51) Int. Cl.
*G01N 1/00*    (2006.01)
*G01N 30/82*    (2006.01)
*G01N 35/10*    (2006.01)
*G01N 30/84*    (2006.01)

(52) U.S. Cl.
CPC .......... *G01N 30/82* (2013.01); *G01N 2035/102* (2013.01); *G01N 2030/8411* (2013.01); *G01N 35/1016* (2013.01)
USPC ....................................... 73/61.56

(58) Field of Classification Search
None
See application file for complete search history.

(56) References Cited

U.S. PATENT DOCUMENTS

| 4,522,237 | A | * | 6/1985 | Endo et al. ...................... 141/95 |
| 4,583,573 | A |   | 4/1986 | Eriksson et al. |
| 5,275,951 | A |   | 1/1994 | Chow et al. |
| 5,655,577 | A | * | 8/1997 | Loen et al. ...................... 141/59 |
| 6,341,629 | B1 | * | 1/2002 | Clark et al. ...................... 141/83 |
| 6,589,791 | B1 |   | 7/2003 | LaBudde et al. |
| 6,610,208 | B1 |   | 8/2003 | Andersson |
| 2006/0211130 | A1 |   | 9/2006 | Macioszek et al. |

FOREIGN PATENT DOCUMENTS

| DE | 42 13 410 | 11/1992 |
| JP | 2004045069 | 2/2004 |
| JP | 2005-227103 | 8/2005 |
| JP | 2008-175791 | 7/2008 |
| WO | WO 99/34931 | 7/1999 |
| WO | WO 00/70337 | 11/2000 |

OTHER PUBLICATIONS

Extended EP Search Report issued Jan. 2, 2014 on corresponding EP application No. 10786453.0.
Office Action issued Dec. 17, 2013 on corresponding JP application No. 2012-514919.

* cited by examiner

*Primary Examiner* — Robert R Raevis

(57) ABSTRACT

A fraction collector comprising a liquid holding means (31) wherein it further comprises a fluid front control arrangement (43) arranged for locating the fluid front at a dispensing nozzle (5) and to control the liquid holding means (31) to keep the fluid front at a predetermined position.

7 Claims, 5 Drawing Sheets

DEVICE FOR REDUCING LOSS OF LIQUID DURING FRACTION COLLECTION

CROSS-REFERENCE TO RELATED APPLICATIONS

This application is a filing under 35 U.S.C. §371 and claims priority to international patent application number PCT/SE2010/050621 filed Jun. 4, 2010, published on Dec. 16, 2010 as WO 2010/144036, which claims priority to application number 0950430-9 filed in Sweden on Jun. 9, 2009.

FIELD OF THE INVENTION

The present invention relates to a device for use with fraction collectors, and more specifically to a device for preventing spillage when switching from one collecting receptacle to the next.

BACKGROUND OF THE INVENTION

Fraction collectors are widely used in many applications, such as in the field of liquid chromatography. A fraction collector is used for dispensing a flow of a liquid to a number of receptacles. The receptacles are typically constituted as test tubes mounted in a rack or as recesses formed in a plate. Two main working principles can be distinguished for fraction collectors: the rotatable collector wherein the receptacles are fed towards a dispensing means by a rotating movement, and the X-Y collector wherein the receptacles are fed towards a dispensing means by linear movements in one or two directions. Of course, these principles are the same as those for fraction collectors wherein the dispensing means is moving while the receptacles are at rest.

Regardless of the type of receptacle or fraction collector working principle, there is always a distance between each separate receptacle. Therefore, when switching from one receptacle to the next, a spillage of the dispensed liquid is likely to occur, especially in a case were the liquid flow is essentially continuous. There are numerous reasons for why such spillage is not desired: it could contain valuable substances, it could be a potential health hazard and the working area becomes messy.

Methods for avoiding the spillage are known. For example, in U.S. Pat. No. 4,077,444 to Gilson et al. there is described a valve and a valve operator that are used to discontinue a liquid flow through a dispensing tube in order to prevent spillage from the tube as it moves between positions. However, in certain applications, such as high precision liquid chromatography, interruption of the liquid flow during a hold time is a disadvantage. The performance of the liquid chromatography system is negatively affected due to the occurrence of diffusion of the components in the liquid volume held in the tubing near the dispensing means during the hold time.

It is also known to use a shunt valve to convey the liquid flow to waste during the receptacle change. This method has obviously the disadvantage that valuable substances may be present in the wasted flow, and consequently are lost.

In JP-A-01068657 a method and device for dispensing column chromatography eluate is described and in JP-A-59026058 a dispensing method and dispensing device are described.

U.S. Pat. No. 6,610,208 discloses a fraction collector that comprises a liquid holding means provided for avoiding loss of liquid during fraction collecting when switching from one collecting receptacle (3) to the next (3') in the fraction collector (1), said liquid holding means comprises an expandable chamber that is actuated during the movement from one receptacle to another in order to stop the output flow from the dispensing nozzle.

However, in some situations when the expandable chamber is actuated to accumulate the flow during the movement, the rate of accumulation might be too high, e.g. due to compensation for errors between actual and reported flow. This may cause air to be drawn from the dispensing nozzle and into the chamber. Thereafter, when the expandable chamber is actuated to dispense the accumulated flow, the mixture of air and fluid in the chamber that is forced out through the nozzle may form bubbles which pops and sends small drops in all directions. These small drops may contaminate the samples in adjacent receptacles and will also accumulate on the sensors and cause malfunction.

Moreover, in fraction collectors wherein the dispensing nozzle is moving while the receptacles are at rest, acceleration of the dispensing nozzle when moving between two receptacles while a drop is still present at the dispensing nozzle may lead to detachment of the drop.

SUMMARY OF THE INVENTION

The object of the invention is to provide a new method for avoiding loss of liquid during fraction collecting and a fraction collector, which method and fraction collector overcomes one or more drawbacks of the prior art. This is achieved by the method and fraction collector as defined in the independent claims.

One advantage with such a method and fraction collector is that it effectively prevents spillage of liquid when switching from one collecting receptacle to the next and that air is drawn into the liquid holding means.

Further scope of applicability of the present invention will become apparent from the detailed description given hereinafter. However, it should be understood that the detailed description and specific examples while indicating preferred embodiments of the invention are given by way of illustration only. Various changes and modifications within the spirit and scope of the invention will become apparent to those skilled in the art from the detailed description below.

Specifically, it should be noted that the use of the method and device of the invention is illustrated within the field of liquid chromatography. However, it is just as useful within any other field of application wherein there is a desire to use a fraction collector without spillage when switching from one collecting receptacle to the next.

DETAILED DESCRIPTION OF THE INVENTION

Figure 1A:
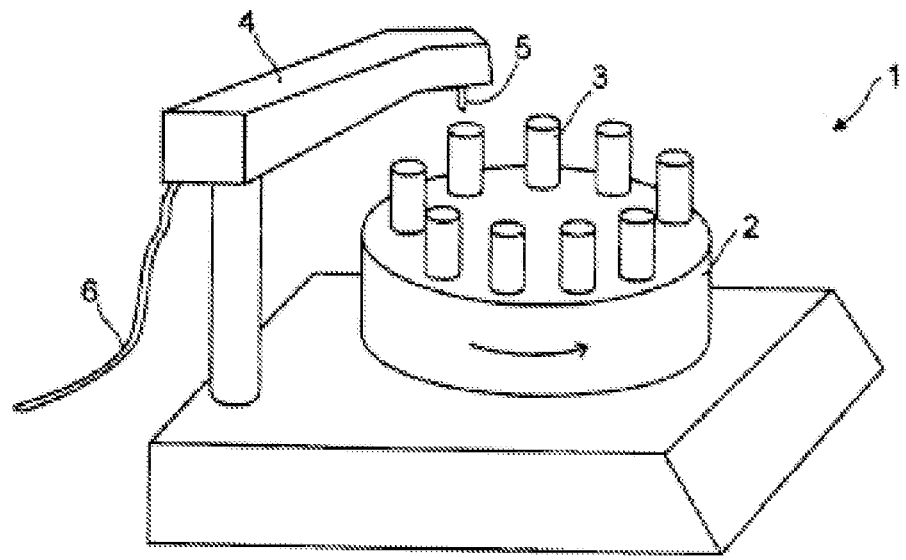
FIGS. 1a and b are schematic perspective views of two types of conventional fraction collectors.
Figure 1B:
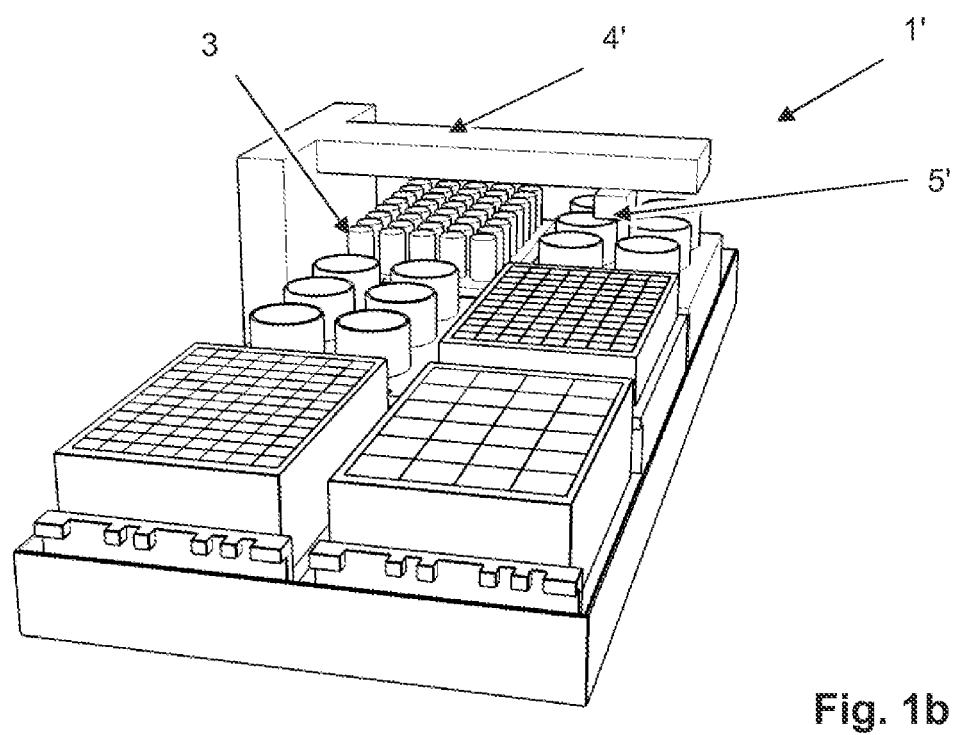

As a background, FIGS. 1a and 1b illustrates schematically the basic components of a typical fraction collector 1. FIG. 1a shows a collector 1 of rotational type, whereas FIG. 1b shows a collector 1' of X-Y translation type. The collector 1 includes a tray 2 that is rotatable around its center (illustrated with an arrow). The tray 2 is provided with a rack for storing receptacles, such as tubes 3. An extension arm 4 holds a dispensing means 5, typically a syringe needle or a plastic tube. The dispensing means is in fluid communication with a feed line, consisting of an inlet tubing 6, through which liquid to be dispensed to the tubes of the fraction collector is provided from any selected equipment (not shown), such as a liquid chromatography column.

During operation, the tray 2 is rotated to place a first tube 3 below the dispensing means 5. Liquid, fed through the tubing 6 via the dispensing means 5, is discharged into the tube. When the first tube 3 has received a fraction volume of liquid, the tray 2 is rotated an angle to place a second tube 3 below the dispensing mean to receive a fraction volume. These steps are repeated a selected number of times.

It should be noted that this general description of components and operating steps of a conventional fraction collector with a rotatable tray is not intended to limit the present invention to this type of fraction collectors. It will be readily understood by anyone skilled in the art that the present invention is just as useful with any other type of conventional fraction collector. For example, a fraction collector wherein the tubes are placed below the dispensing device using linear movements of the dispensing nozzle like in FIG. 1b, or wherein other types of receptacles than test tubes, such as microtiter plates are used could be used with the invention, as is schematically illustrated by FIG. 1b.

Regardless of the type of fraction collector, there is a time interval T between the moment when the first receptacle leaves the liquid flow discharged from the dispensing means and the moment when the next receptacle is in place to receive the liquid flow. Assuming that the flow rate is FR(t), wherein t indicates that the flow rate could be varying with time, a volume V is lost during the receptacle switch, provided that no measures are taken. This volume may be calculated using the formula $$V = \int_0^T FR(t) \cdot dt \quad [1]$$

One conventional approach to avoid the spillage is to stop the flow through the dispensing means by way of a shut-off valve. Thereby no liquid is lost, but halting the flow affects the equipment upstream of the fraction collector, as well as the precision of the separation in its entirety.

According to a first aspect of the present invention the spillage is avoided, at the same time as no liquid loss occurs, by performing the steps of
1) actuating an expandable chamber to accumulate the liquid flow during the time interval for switching from a first to a second receptacle,
2) locating the fluid front in the nozzle,
3) controlling the actuation of the expandable chamber to keep the fluid front at a predetermined position,
4) actuating the expandable chamber to dispense the accumulated liquid into the second receptacle.

One embodiment of a device for use with the method of the invention is illustrated in FIG. 2a-d, showing an arrangement including one embodiment of a liquid holding means 31 and a fluid front control arrangement 43. According to the disclosed embodiment, the fluid front control arrangement 43 comprises a fluid front detector 40 and a fluid front control unit 42. The fluid front detector 40 may be of any suitable type, capable of reliably locating the fluid front. Examples of fluid front detector 40 are disclosed in FIGS. 3 to 5 and are discussed more in detail below. In FIG. 2a-d, the control unit 42 is schematically disclosed as a separate control unit, it may however be integrated with a controller controlling other functions of the collector 1, e.g. the liquid holding means 31.

In FIG. 2a-d, the liquid holding means 31 comprises an expandable chamber 34 defined by the inner wall of a hollow cylindrical body 41, an end plate 49 and a piston member 37.

The end plate 49 is provided with two openings, an inlet opening connected to input tubing 6 and an outlet opening connected to dispensing means or nozzle 5. In FIGS. 2a-d the inlet opening is shown as being arranged at the top section of the expandable chamber 34 and the outlet opening at the lower. However in practice the outlet opening is preferably arranged at the top of the expandable chamber in order to evacuate air bubbles that may enter the system. Furthermore, a shaft 35 is provided. Said shaft being controllably and reciprocally moveable in the axial direction of the cylindrical body 41. The shaft 35 and the piston member 37 are fixed to each other, for example by a threaded joint, so as to be movable as one unit.

A drive unit 36, such as a linear stepping motor controlled by a microprocessor, controls the displacement of the shaft 35, and consequently of the piston member 37.

The piston member 37 is provided with suitable sealing means or the like on its cylindrical surface to seal against the inner wall of the cylindrical body 41.

The expandable chamber 34 is formed so that there is provided a fluid path between the inlet opening and the outlet opening when the piston member 37 is in it its extreme left position, i.e. when the expandable chamber is "inflated", to allow the liquid to pass through the expandable chamber 34 in this stage.

Figure 2A:
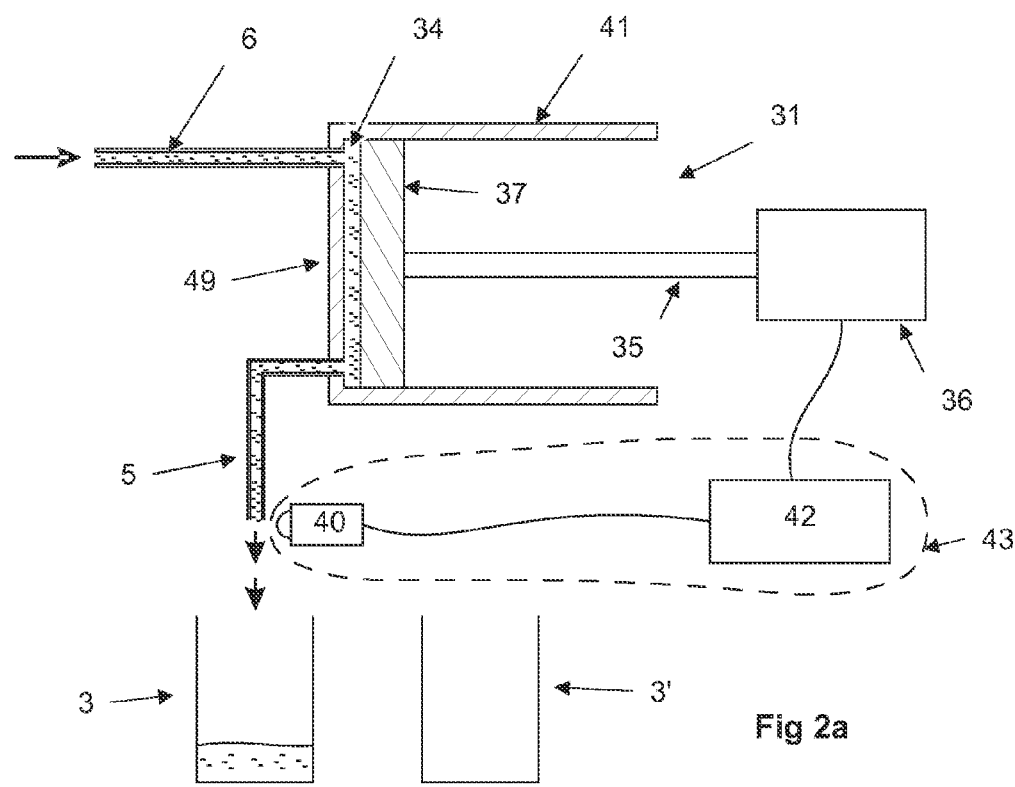
FIG. 2a-d are schematic views illustrating flow paths and a device according to one embodiment of the present invention, in four operating positions.

FIG. 2A schematically illustrates a first state wherein the piston member 37 of the expandable chamber 34 is in its extreme left position, representing the case wherein liquid being fed via the input tubing 6 is discharged to a receptacle 3 via dispensing nozzle 5. In this state, the fluid front control arrangement 43 is essentially inactive.

Figure 2B:
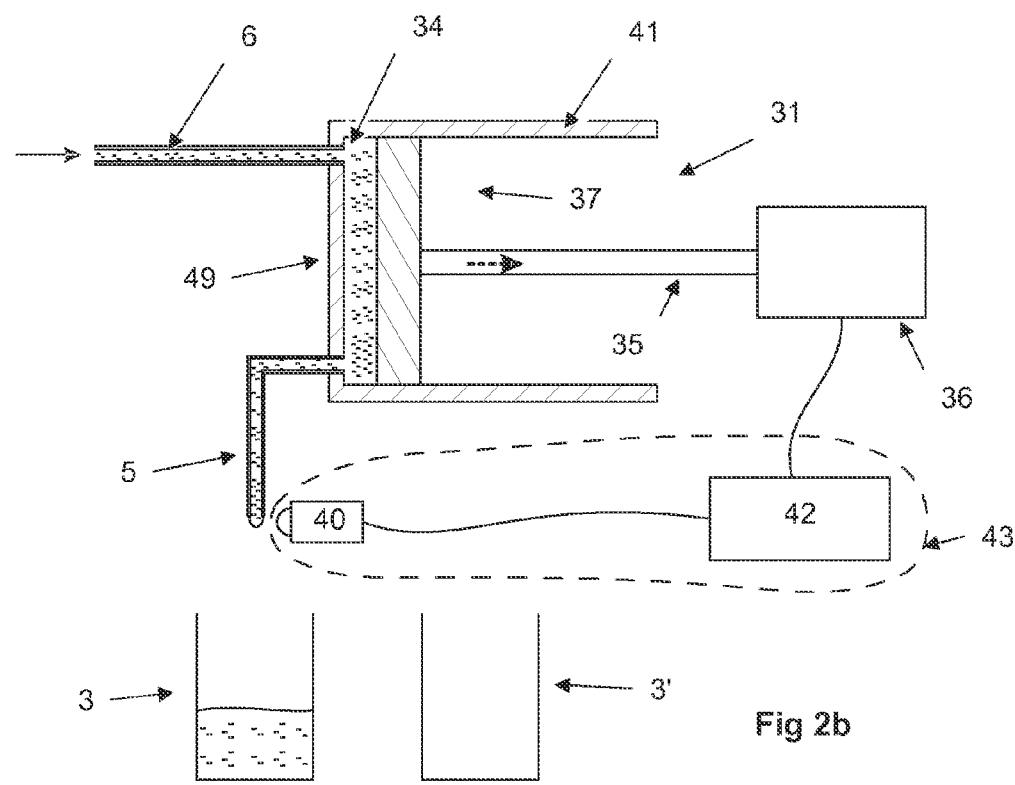
Figure 2C:
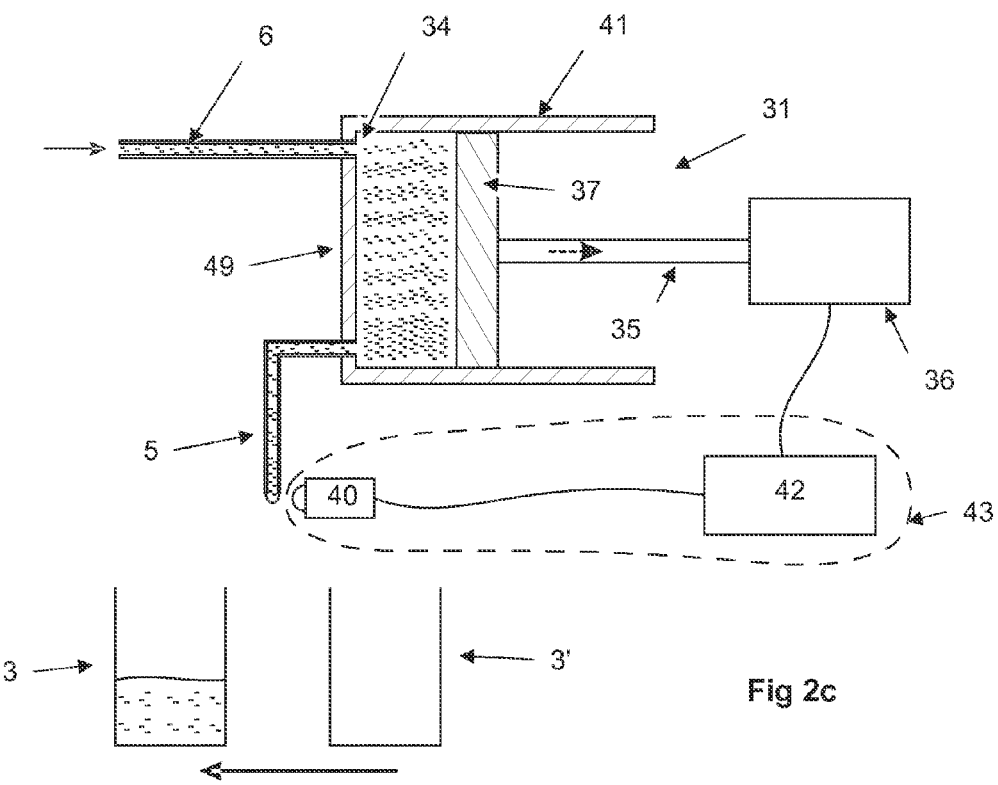

FIG. 2B schematically illustrates a second state occurring during initial part of the time interval T for switching from on receptacle 3 to the next receptacle 3'. In this second state, the piston member 37 is pulled backwards by the drive unit 36 acting on the piston shaft 35. The liquid coming from the input tubing 6 is thereby accumulated in the expanding chamber 34 of the liquid holding means 31, while no liquid is discharged through the dispensing nozzle 5. In this state, the fluid front detector 40 is arranged to locate the fluid front at the nozzle 5, and the fluid front control unit 42 is arranged to control the drive unit 36 to move the piston member 37 at a speed that essentially keeps the fluid front at a predetermined position at the nozzle 5. In one embodiment wherein the liquid flow from the nozzle 5 is in the form of drops (as schematically indicated in FIG. 2a, the fluid front detector 40 may be arranged to detect when a drop is dispensed and the fluid front control unit 42 to activate the liquid holding means 31 in response thereto to establish the predetermined fluid front position essentially instantaneously. In case the liquid flow from the nozzle 5 is in the form of a continuous flow, then the fluid front control unit 42 may be arranged to activate the liquid holding means 31 to reduce the flow from the nozzle 5 to a drip flow of suitable frequency as detected by the fluid front detector 40, prior to establishing the predetermined fluid front position in accordance with above. When the fluid front control arrangement 43 has reached this state, the movement to the next receptacle 3' may be performed, as is disclosed in FIG. 2c. During the movement, the fluid front control arrangement 43 keeps controlling the fluid front position. For fraction collectors 1 with a static dispensing nozzle, the predetermined fluid front position may be any suitable position ensuring that no air enters the expanding chamber 34 of the liquid holding means 31 and that no drop is released from the nozzle. However, for fraction collectors 1 with a moving dispensing nozzle 5, the predetermined fluid front position need to be positioned so that no drop is detached upon acceleration of the dispensing nozzle when moving between two receptacles.

Figure 2D:
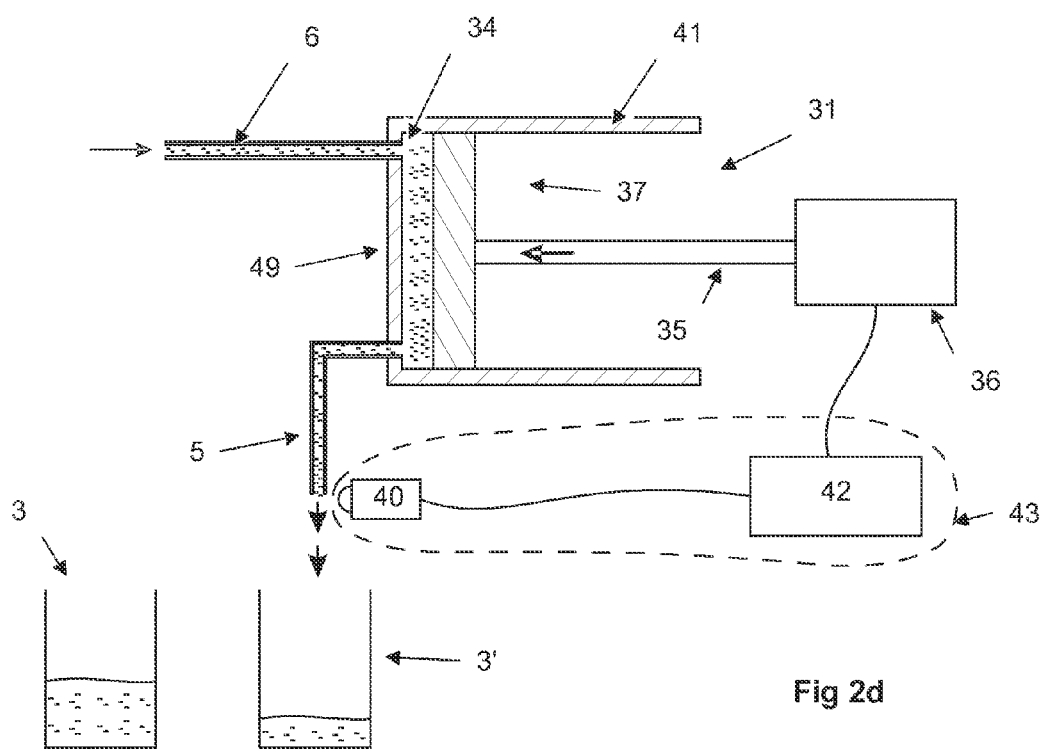

FIG. 2d schematically illustrates a fourth state occurring after the moment when the next receptacle 3' is situated below the dispensing nozzle 5. In this third state, the piston member 37 is pushed forward by the drive unit 36 acting on the piston shaft 35. The liquid accumulated in the chamber 34 is pressed out through the outlet opening to the next receptacle 3' via the dispensing nozzle 5. Simultaneously, liquid being fed from the input tubing 6 is also discharged to the next receptacle 3' via the chamber 34 and the dispensing nozzle 5. This fourth state is present until the piston element is returned to its extreme left position, wherein the first state according to FIG. 2a occurs. In this state, the fluid front control arrangement 43 is essentially inactive.

When designing a liquid holding device according to the present invention, measures and materials for the different components of the device have to be selected based on the requirements put by the application at hand, as is natural for anyone skilled in the art. However, certain principles have to be taken into consideration when designing a device according to the first embodiment of the present invention.

Thus, the piston member 37 is controlled to be pulled out at a rate corresponding very close to the flow rate in the inlet tubing 6, i.e. the liquid volume being fed through the inlet tubing per time unit (as calculated with a formula such as the eq. [I]0 above) always is substantially equal to the volume created in the expanding chamber 34. In this way, the fluid front is prevented from being sucked into the dispensing nozzle and from the expandable chamber, at the same time as dripping or spilling in between the receptacles 3 and 3'.

Furthermore, the piston member 37 should be pushed forward at a rate correlated to the pressure in the inlet tubing 6, as well as to the flow-through capacity of the outlet opening, such that the flow from the inlet tubing will pass through the chamber 34 virtually undisturbed at the same time as the liquid volume previously held in the chamber is discharged to the dispensing means. Otherwise, the resolution of separated substances within the liquid could be negatively affected.

Figure 3A:
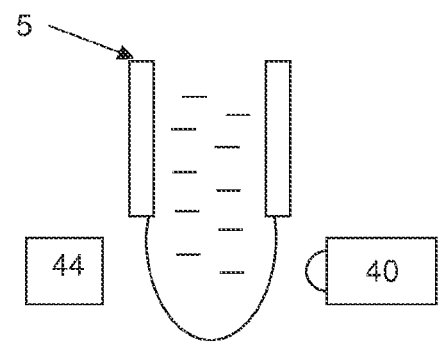
FIGS. 3a and 3b are schematic views of one embodiment of a drop sensor.
Figure 3B:
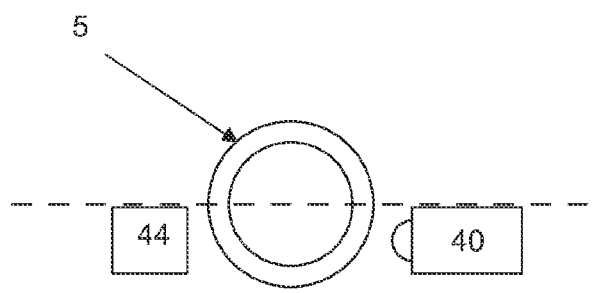

FIGS. 3a and 3b schematically show one embodiment of a fluid front detector 40 further comprising a light source 44 arranged to direct light towards the fluid front detector 40 being arranged to detect the so received light. As can be seen in the figures, the light source 44 and the detector are arranged at opposite positions with respect to the nozzle 5, whereby a drop at the end of the nozzle will reduce the amount of light that reaches the detector compared to when no drop is present. According to one embodiment, the light source is a LED and the detector any suitable light detecting means. According to one embodiment, shown in FIG. 3b, which is a bottom view of the nozzle and the fluid front sensor arrangement 40, 44, the sensor arrangement is arranged off axis in order to avoid reflection problems that may arise when the sensor is arranged on the on the center-axis.

Figure 4:
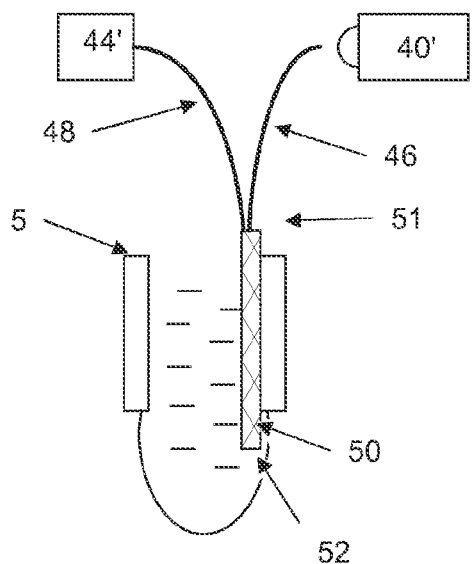
FIG. 4 is a schematic view of one embodiment of another drop sensor.

FIG. 4 discloses a fluid front sensor arrangement 43 based on fiber optics. The sensor arrangement is utilizing the difference in intensity of Frenell reflections at the interface between air and the end of a Synthetic Fused Silica (SFS) Fiber or the like, and buffer and said end. The disclosed embodiment comprises a light source 44' e.g. a bright red LED is coupled to an optical fiber 48 that guides the light to a sensor fiber 50 via a beamsplitter 51. The sensor fiber is arranged with a terminating end surface 52 at the dispensing nozzle 5 and in the disclosed embodiment the end surface 52 protrudes through the nozzle where the liquid is dispensed out e.g. drop by drop. When the drop just has fallen there is air at the end surface 52. The reflected intensity, (R), at that interface can be calculated by Frenell's equation:

$$R=(n_1-n_2)^2/(n_1+n_2)^2$$

Where $n_1$ is the index of refraction of SFS,=1.55 @ 600 nm, and $n_2$ is the index of refraction of air=1.00 or buffer=1.33 (water @ 600 nm). For air R is 4.6% of incoming intensity and for buffer R is 0.58%, so it will be a difference in reflected intensity by a factor of almost 8. The reflected intensity is guided back in the sensor fiber to a collecting fiber 46 at the beamsplitter 51. The collecting fiber 46 guides the light to an optical detector 40, e.g. a photo diode, and the intensity is measured.

Figure 5:
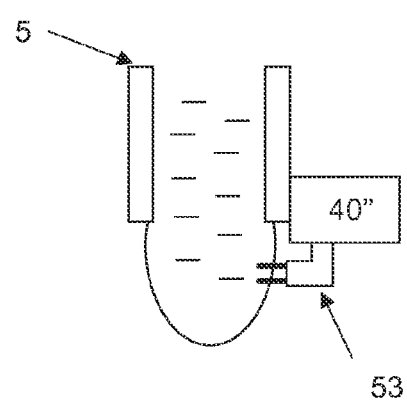
FIG. 5 is a schematic view of one embodiment of still another drop sensor.

FIG. 5 discloses a fluid front sensor arrangement 43 based on conductivity detection wherein the sensor 40" comprises an electrode arrangement 53 for measuring the conductivity at the dispensing nozzle 5 to detect the presence of liquid or not.

In addition to a device according to the invention, a system utilizing the method of the invention, such as a liquid chromatography system including a fraction collector, should also include control means for correlating the operation fluid front control arrangement 43, the liquid holding means 31 and the fraction collector. This control means could be established by any suitable means, such as a personal computer together with suitable interface circuits commonly known within the art.

Figure 6:
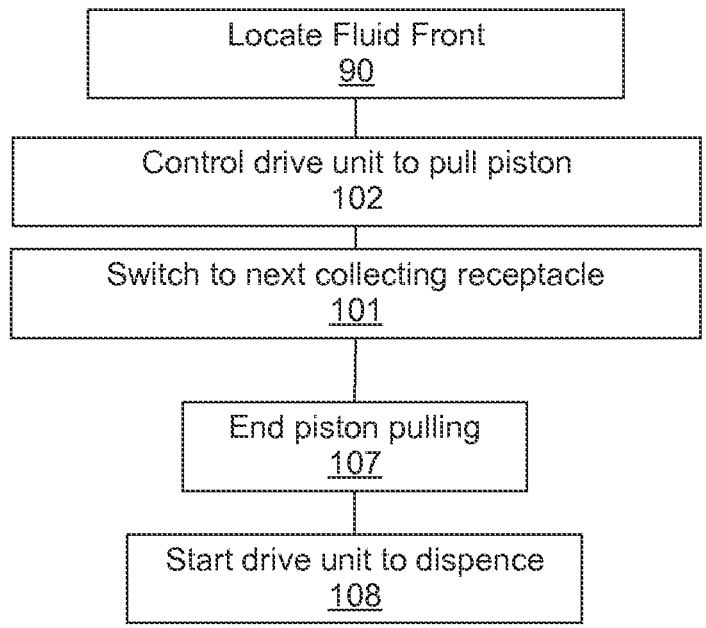
FIG. 6 is a flow chart showing the operation of a control means for controlling a fraction collector and liquid holding means according to the present invention.

A flow chart, showing control steps to be executed by such a control means is shown in FIG. 6. Depending on the application, different types of criteria for initiating the switching of receptacles could be used such as detecting a liquid level in a receptacle, calculate a delivered liquid volume, monitoring a property significant for substances transported in the liquid etc.

Regardless of the criteria selected, the control means begins the receptacle switching by locating the fluid front 90 and controlling the drive unit to pull piston 102 to position the fluid front at a predetermined position. The following step is to switch to the next collecting receptacle 101. When the next collecting receptacle is in correct position with respect to the dispensing nozzle 5 the control means stops 107 the drive unit 36 from pulling the piston element. At that moment, liquid from the inlet tubing 6 flows towards the dispensing means 5 via the outlet opening.

Next, the control means commands the drive unit to push the piston 108 to compress the chamber, thereby dispensing the content of the chamber through the dispensing nozzle 5.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Of course, it should also be realized that although liquid chromatography has been used as a suitable example of a field of application, the application of the method and the device of the invention is not restricted to this field.

What is claimed is:

1. A method for avoiding loss of liquid during fraction collection of a liquid flow when switching from one collecting receptacle to the next in a fraction collector, comprising the steps:
  actuating an expandable chamber to accumulate the liquid flow during the time interval for switching from one collecting receptacle to the next receptacle,
  locating the fluid front at a dispensing nozzle,
  controlling the actuation of the expandable chamber to keep the fluid front at a predetermined position,
  actuating the expandable chamber to dispense the accumulated liquid into the second receptacle.

2. A fraction collector comprising: a liquid holder including an expandable chamber; a dispensing nozzle in fluid communication with said chamber; a fluid front sensor at said nozzle for sensing a fluid front; and a fluid front control arrangement arranged to control the liquid holder to keep the fluid front at a predetermined position at the nozzle.

3. The fraction collector of claim 2, wherein the fluid front sensor comprises an optical fluid front detector.

4. The fraction collector of claim 3, wherein the optical fluid front detector comprises a light source directing light across a fluid flow path at the nozzle and an optical detector arranged to receive said light.

5. The fraction collector of claim 4, wherein the light source and the optical fluid front detector are arranged off axis with respect to the center of the nozzle.

6. The fraction collector of claim 3, wherein the optical fluid front detector comprises a light source arranged to couple light to an optical sensor fiber arranged with a terminating end surface in the fluid flow path at the dispensing nozzle, and an optical detector arranged to register the reflected intensity of light from the end surface.

7. The fraction collector of claim 2, wherein the fluid front sensor comprises a conductivity fluid front detector (40).

* * * * *